United States Patent [19]

Takano

[11] Patent Number: 4,578,582

[45] Date of Patent: Mar. 25, 1986

[54] RADIATION IMAGE RECORDING AND REPRODUCING SYSTEM WITH PREFERENTIAL PROCESSING FUNCTION

[75] Inventor: Masao Takano, Kanagawa, Japan

[73] Assignee: Fuji Photo Film Co., Ltd., Kanagawa, Japan

[21] Appl. No.: 435,203

[22] Filed: Oct. 19, 1982

[30] Foreign Application Priority Data

Oct. 27, 1981 [JP] Japan .............................. 56-171767

[51] Int. Cl.⁴ ............................................. G01T 1/105
[52] U.S. Cl. ................................. 250/327.2; 271/298
[58] Field of Search ..................... 250/327.2; 271/298, 271/300, 301

[56] References Cited

U.S. PATENT DOCUMENTS

| | | | |
|---|---|---|---|
| 3,724,657 | 4/1973 | Katagiri et al. | 198/366 |
| 3,807,553 | 4/1974 | Billett et al. | 209/565 |
| 4,192,607 | 3/1980 | Hage | 355/50 |
| 4,236,078 | 11/1980 | Kotera et al. | 250/327.2 |
| 4,239,968 | 12/1980 | Kotera et al. | 250/327.2 |
| 4,258,264 | 3/1981 | Kotera et al. | 250/484.1 |
| 4,273,326 | 6/1981 | Snellman et al. | 271/288 |
| 4,276,473 | 6/1981 | Kato et al. | 250/327.2 |
| 4,302,673 | 11/1981 | Bly | 250/332 |
| 4,310,886 | 1/1982 | Kato et al. | 364/414 |
| 4,315,318 | 2/1982 | Kato et al. | 382/6 |
| 4,346,295 | 8/1982 | Tanaka et al. | 250/327.2 |
| 4,368,384 | 1/1983 | Kato et al. | 250/205 |
| 4,387,428 | 6/1983 | Ishida et al. | 364/414 |
| 4,394,581 | 7/1983 | Takahashi et al. | 250/484.1 |
| 4,410,799 | 10/1983 | Okamato | 250/327.2 |

Primary Examiner—Alfred E. Smith
Assistant Examiner—Constantine Hannaher
Attorney, Agent, or Firm—Sughrue, Mion, Zinn, Macpeak and Seas

[57] ABSTRACT

In a radiation image recording and reproducing system in which a radiation image is once recorded on a stimulable phosphor sheet and then read out and reproduced to a visible image, a phosphor sheet carrying a radiation image to be processed urgently is preferentially sent to an image read-out section to reproduce the image. A by-pass feeding line for by-passing a stacker installed on a sheet feeding line to store the phosphor sheets and send them one by one to the image read-out section is positioned on the sheet feeding line. A feeding line switching mechanism is positioned at the junction between the by-pass feeding line and a line connected to the stacker to make the sheet feeding line communicate with the by-pass feeding line in response to a preferential processing signal sent from a general controller. The sheet feeding line and the by-pass feeding line may be formed of belt conveyors, and the switching mechanism may comprise a movable plate.

14 Claims, 4 Drawing Figures

RADIATION IMAGE RECORDING AND REPRODUCING SYSTEM WITH PREFERENTIAL PROCESSING FUNCTION

BACKGROUND OF THE INVENTION

1. Field of the Invention

This invention relates to a radiation image recording and reproducing system for once recording a radiation image on a stimulable phosphor sheet, scanning the stimulable phosphor sheet with a stimulating ray which causes it to emit light in the pattern of the radiation image stored therein, reading out and converting the emitted light to an electric signal, and then reproducing a visible image by use of the electric signal. More particularly, this invention relates to a radiation image recording and reproducing system in which a particular stimulable phosphor sheet can be sent to an image read-out section in preference to another phosphor sheet and the radiation image stored on said particular phosphor sheet can preferentially be reproduced to a visible image.

2. Description of the Prior Art

When certain kinds of phosphors are exposed to such radiation as X-rays, α-rays, β-rays, γ-rays or ultraviolet rays, they store a part of the energy of the radiation. Then, when the phosphor which has been exposed to the radiation is exposed to a stimulating ray such as visible ray, light is emitted from the phosphor in the pattern of the stored energy of the radiation. A phosphor exhibiting such properties is referred to as a stimulable phosphor.

As disclosed in U.S. Pat. Nos. 4,258,264 and 4,276,473, 4,346,295 and 4,387,428, Japanese Unexamined Patent Publication No. 56(1981- )11395, it has been proposed to use the stimulable phosphor for recording a radiation image. Specifically, the stimulable phosphor is first exposed to a radiation to have a radiation image stored therein, and is then scanned with a stimulating ray which causes it to emit light in the pattern of the stored image. The light emitted from the stimulable phosphor upon stimulation thereof is photoelectrically detected and converted to an electric image signal, which is processed as desired to reproduce an image of a quality suitable for viewing and diagnostic purposes. The image finally obtained may be reproduced as a hard copy or on a cathode ray tube (CRT).

When the radiation image recording and reproducing method described above is practically used for medical diagnosis, the stimulable phosphor sheet provided with a stimulable phosphor layer is used, in general, in the form in which it is held in a case such as a cassette for containing a stimulable phosphor sheet or a magazine for containing several phosphor sheets. In hospitals and the like, since a great number of images must be processed quickly, it is preferable to use a sheet feeder for receiving the case containing a stimulable phosphor sheet or sheets, automatically taking up each sheet from the case and sending it to a line for feeding it to an image read-out section, or to use an image input table or stand provided therein with such a sheet supplying mechanism.

In many large hospitals and the like, it is necessary to use a plurality of image input stands respectively designed for recording a radiation image by use of the cassette or the magazine. Further it is practicable that each image input stand can work with stimulable phosphor sheets of several different sizes according to the portions of an object to be recorded. Therefore, a plurality of sheet feeders will also be used according to the kinds of the image input stands and the sizes of the stimulable phosphor sheets.

In order to put the above-mentioned radiation image recording and reproducing method into practice in hospitals, a stacker for temporarily storing the stimulable phorphor sheets sent from the image input section and sequentially feeding the sheets one by one to the image read-out section must be used unless the processing capacity in the image read-out section and the subsequent sections is always equal to or larger than the number of stimulable phosphor sheets sent from the image input stands. The stacker is required particularly when only one image read-out apparatus is used for many image input stands and sheet feeders. However, the stacker is necessary also when there are many image read-out apparatuses since the processing load sometimes exceeds the capacity of the image read-out apparatus if there are a great number of patients coming to consult the radiologist at a time. This also applies when an image read-out apparatus is used for a set of the image input stand and the sheet feeder.

In hospitals, it often happens that a radiation image of a particular patient should be urgently reproduced to a visible image in preference to that of another patient. However, in the radiation image recording and reproducing system using the image input stand, the sheet feeder, and the stacker for receiving the stimulable phosphor sheets from the sheet feeding line and sequentially sending the sheets to the image read-out apparatus, even if the image input stand is preferentially used for the particular patient and the stimulable phosphor sheet carrying the radiation image of the patient is quickly sent to the sheet feeder, the phosphor sheet cannot be quickly fed from the sheet feeder to the sheet feeding line when another sheet feeder is feeding other phosphor sheets therefrom to the sheet feeding line. Further, even when the stimulable phosphor sheet carrying the radiation image to be preferentially processed is fed to the stacker via the sheet feeding line, the radiation image cannot be read out before all phosphor sheets already existing in the stack zone of the stacker have been processed in the image read-out apparatus. Thus, in the above-mentioned radiation image recording and reproducing method, it is impossible to preferentially process a particular stimulable phosphor sheet.

SUMMARY OF THE INVENTION

The primary object of the present invention is to provide a radiation image recording and reproducing system in which a stimulable phosphor sheet supplying means and a stacker containing a stack zone are used.

Another object of the present invention is to provide a radiation image recording and reproducing system highly suitable for medical diagnosis in hospitals.

The specific object of the present invention is to provide a radiation image recording and reproducing system having the preferential processing function for very quickly processing a paticular stimulable phosphor sheet in preference to another phosphor sheet.

The radiation image recording and reproducing system provided with the preferential processing function in accordance with the present invention comprises a by-pass feeding line for by-passing the stack zone in the sheet feeding line mentioned above, and a feeding line switching mechanism for making the sheet feeding line communicate with the by-pass feeding line in response to a preferential processing signal. The system can very quickly reproduce a radiation image stored on a stimulable phosphor sheet to be preferentially processed to a visible image in preference to other phosphor sheets. Accordingly, the system is practically very advantageous for medical diagnosis in hospitals in which it often happens that some radiation images should be very quickly processed and reproduced to visible images for viewing and diagnostic purposes in preference to other radiation images.

In the present invention, a sheet supplying means is employed to supplying the stimulalbe phosphor sheets carrying radiation images stored therein one at a time to the sheet feeding line connected to an image read-out section. The sheet supplying means may, for example, be a means for receiving a case such as a cassette containing a stimulable phosphor sheet or a magazine containing a plurality of phosphor sheets, automatically taking the stimulable phosphor sheets from the case, and sending the sheets one by one to the sheet feeding line connected to the image read-out section. It is practically preferable that the sheet supplying means is a sheet feeder discrete from the image input stand, or a similar mechanism incorporated in the image input stand.

In the present invention, the stimulable phosphor sheet is provided with a layer of a stimulable phosphor. The stimulable phosphor has such properties that, when exposed to such radiation as X-rays, α-rays, β-rays, γ-rays or ultraviolet rays, the stimulable phosphor stores a part of the energy of the radiation. Then, when the phosphor which has been exposed to the radiation is exposed to a stimulating ray such as visible ray, light is emitted from the phosphor in the pattern of the stored energy of the radiation.

In the present invention, in order to improve the signal-to-noise ratio, it is preferable that the stimulable phosphor emits light having a wavelength range not overlapping the range of wavelength of the stimulating ray employed to excite the stimulable phosphor. Preferably, the stimulable phosphor should emit light having a wavelength within the range between 300 nm and 500 nm, and the wavelength of the stimulating ray should be within the range between 600 nm and 700 nm, as disclosed in U.S. Pat. No. 4,258,264.

As the stimulable phosphor capable of emitting light having a wavelength within the range between 300 nm and 500 nm, for example, rare earth activated alkaline earth metal fluorohalide phosphor is preferred. One example of this phosphor is, as shown in DE-05-2,928,245 a phosphor represented by the formula $(Ba_{1-x-y},Mg_x,Ca_y)FX:aEu^{2+}$ wherein X is at least one of Cl and Br, x and y are numbers satisfying $0<x+y\leq0.6$ and $sy\neq0$, and a is a number satisfying $10^{-6}\leq a\leq 5x10^{-2}$. Another example of this phosphor is, as shown in U.S. Pat. No. 4,239,968 a phosphor represented by the formula $(Ba_{1-x},M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0\leq x\leq 0.6$, and y is a number satisfying $0\leq y\leq 0.2$. Further, as the stimulable phosphor to be used in this invention can be used ZnS:Cu,Pb; $BaQ.xAl_2O_3$:Eu wherein $0.8\leq x\leq 10$; and $M^{II}O\ xSiO_2$:A wherein $M^{II}$ is Mg, Ca, Sr, Zn, Cd or Ba, A is Ce, Tb, Eu, Tm, Pb, Tl, Bi or Mn, and x is a number satisfying $0.5\leq x\leq 2.5$, as shown in U.S. Pat. No. 4,236,078. Furthermore, as the stimulable phosphor can be used LnOX:xA wherein Ln is at least one of La, Y, Gd and Lu, X is at least one of Cl and Br, A is at least one of Ce and Tb, x is a number satisfying $0<x<0.1$, as shown in U.S. Pat. No. 4,236,078. Among the above numerated phosphors, the rare earth activated alkaline earth metal fluorohalide phosphor is the most preferable, among which barium fluorohalides are the most preferable in view of the high intensity of emission of light.

Further, barium fluorohalide phosphors added with a metal fluoride as disclosed in European Patent No. 21,342, or barium fluorohalide phosphors containing at least one of a metal chloride, a metal bromide and a metal iodide as disclosed in U.S. patent application Ser. No. 209,208 are also preferable because of their improved light emitting characteristics.

It is also desirable to color the phosphor layer of the stimulable phosphor sheet made of the above phosphor by use of pigments or dyes to improve the sharpness of the image obtained thereby as disclosed in U.S. Pat. No. 4,394,581.

DESCRIPTION OF THE PREFERRED EMBODIMENTS

The present invention will hereinbelow be described in further detail with reference to the accompanying drawings.

Figure 1:
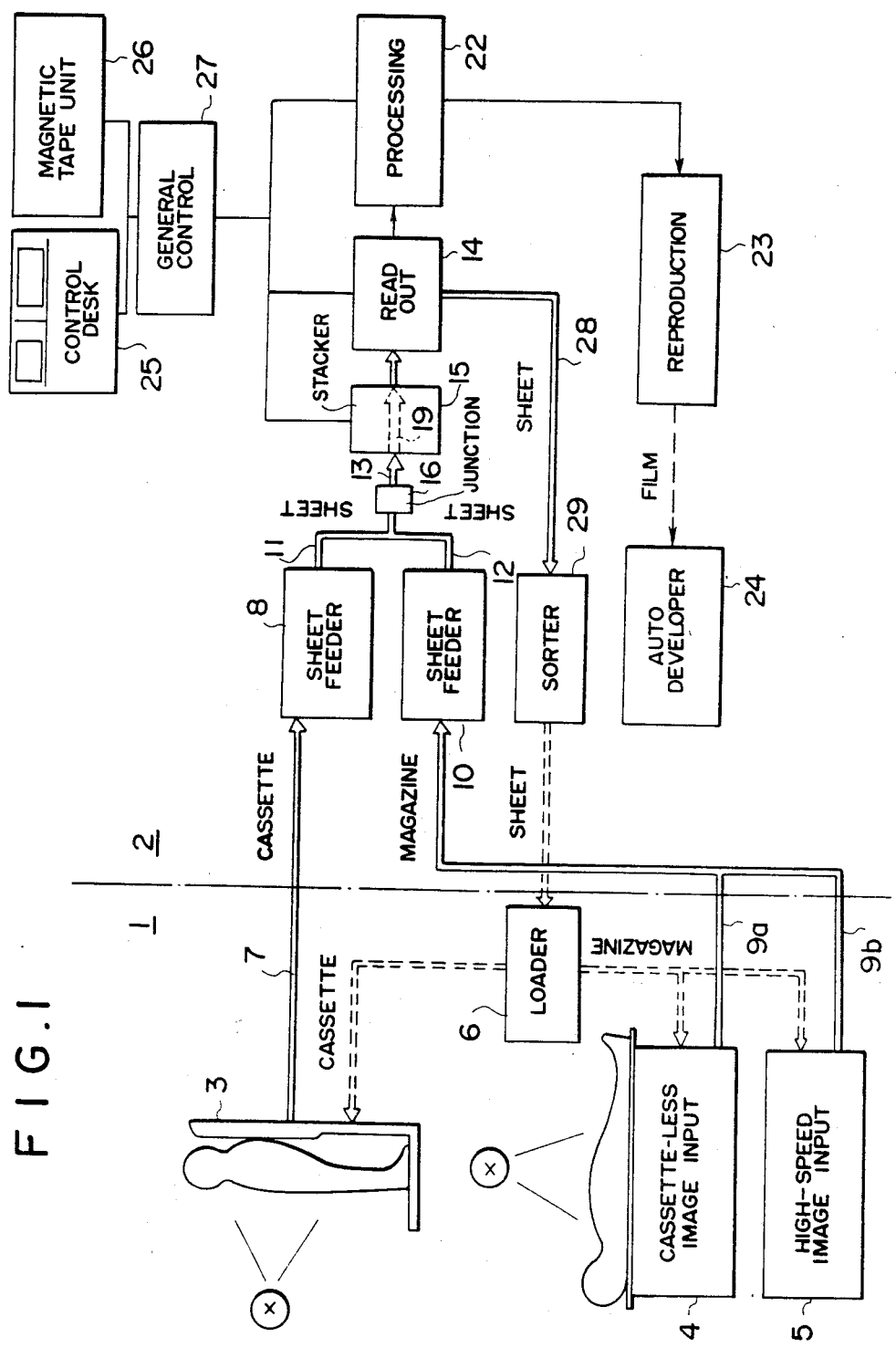
FIG. 1 is a schematic diagram showing an embodiment of the radiation image recording and reproducing system in accordance with the present invention.

Referring to FIG. 1 showing an embodiment of the radiation image recording and reproducing system in accordance with the present invention, which is adopted for medical diagnosis in a hospital, the system consists of an image input compartment 1 and an image reproducing compartment 2 as divided by a one-dot chain line in the figure. In FIG. 1, the doubleline arrow indicates the movement of stimulable phosphor-sheets, and the single solid line indicates the flow of electric signals. In the image input compartment 1 are positioned a cassette type image input stand 3 for recording a radiation image by use of a cassette containing one stimulable phosphor sheet, a cassetteless type image input stand 4 for recording a radiation image by use of a magazine containing a plurality of phosphor sheets, a high-speed image input apparatus 5 for conducting recording by using such a magazine, and a loader 6 for loading the phosphor sheets into the cassettes and magazines. After a radiation image is recorded on a stimulable phosphor sheet at the cassette type image input stand 3, the cassette containing the phosphor sheet is sent to a sheet feeder 8 positioned in the image reproducing compartment 2 via a cassette feeding line 7. The cassette feeding line 7 may be realized by manual cassette transfer or a known automatic feeding means such as a belt conveyor or an air chute.

On the other hand, the magazines containing the stimulable phosphor sheets carrying radiation images recorded thereon at the cassette-less image input stand 4 and the high-speed image input apparatus 5 are sent to a sheet feeder 10 positioned in the image reproducing compartment 2 via magazine feeding lines 9a and 9b, which join together into one line connected to the sheet feeder 10. The magazine feeding lines 9a and 9b may be formed in the same way as the cassette feeding line 7. In general, however, the magazines are manually taken out of the image input stand 4 and the apparatus 5 and inserted into the sheet feeder 10 by a radiographic technician. The sheet feeders 8 and 10, respectively, take the stimulable phosphor sheets out of the cassettes and the magazines and send the phosphor sheets to sheet feeding lines 11 and 12. The sheet feeding lines 11 and 12 are joined together and connected to a sheet feeding line 13. These sheet feeding lines 11, 12, and 13 are constituted by automatic conveying means, for example, belt conveyors, which can send the bare stimulable phosphor sheets taken out of the cassettes and magazines to an image read-out apparatus 14 without damaging the phosphor sheets. On the sheet feeding line 13 is positioned a stacker 15 provided with a stack zone for storing the stimulable phosphor sheets sent along the line 13 and sequentially sending the phosphor sheets one by one to the image read-out apparatus 14. The stacker 15 is also provided with a by-pass feeding line for by-passing the stack zone, and a feeding line switching mechanism positioned at the junction between the by-pass feeding line and the line connected to the stack zone. Like the sheet feeding lines 11, 12 and 13, the by-pass feeding line is constituted by an automatic feeding means, for example, a belt conveyor.

In the image read-out apparatus 14, each stimulable phosphor sheet is scanned with a stimulating ray, e.g. a laser beam, which causes it to emit light in the pattern of the stored image, and the emitted light is photoelectrically detected and converted to an electric signal. The image read-out apparatus 14 consists of a source of the stimulating ray, a scanning means including a light deflector and a linear movement mechanism, a photodetector such as a photomultiplier for reading out the light emitted from the stimulable phosphor upon stimulation thereof, a light transfer means for transferring the emitted light to the photodetector, and the like.

The image read-out apparatus 14 may be of the type as disclosed in Japanese Unexamined Patent Publication No. 56(1981)-11395 U.S. Pat. Nos. 4,368,384 and 4,410,799. The light transfer means may be of a material and a configuration as described in U.S. Pat. No. 4,346,295, and installed as disclosed in U.S. Pat. appln. Ser. No. 105,240.

The electric image signal obtained from the image read-out apparatus 14 is then converted to an image reproducing signal by an image processing section 22 and sent to an image reproducing apparatus 23. To obtain a radiation image having a high diagnostic efficiency and accuracy, the electric image signal is preferably processed in various ways in the image processing section 22. For example, the frequency of the image signal may be processed as disclosed in U.S. Pat. Nos. 4,315,318, 4,346,295 and 4,387,428 and the gradation may be processed as disclosed in U.S. Pat. Nos. 4,302,673, 4,276,473 and 4,310,886. In the image reproducing apparatus 23, a photographic film is exposed to light modulated with the reproducing signal. The photographic film is then developed to yield a hard copy of the radiation image in an automatic developing apparatus 24. The radiation image may, of course, be reproduced in any other ways, for example may be reproduced to a visible image on a CRT by use of the reproducing signal. The image read-out apparatus 14, the stacker 15 and the image processing section 22 are controlled by a general control section 27 connected, for example, to a control desk 25, magnetic tape apparatus 26 for storing the image information in the memory, and the like. In this embodiment, after the radiation images are read out from the stimulable phosphor sheets in the image read-out apparatus 14, the phosphor sheets are sent to a sorter 29 via a sheet return line 28 and sorted according to the sheet sizes by the sorter 29. The sorted phosphor sheets are returned to the loader 6, appropriately processed and reused for recording radiation images.

Figure 2:
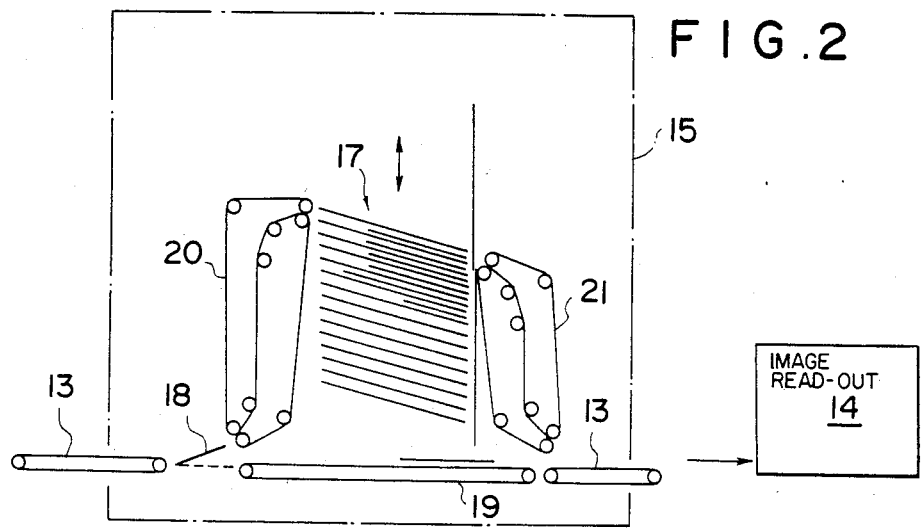
FIGS. 2, 3A and 3B are schematic diagrams showing parts of the system shown in FIG. 1.
Figure 3A:
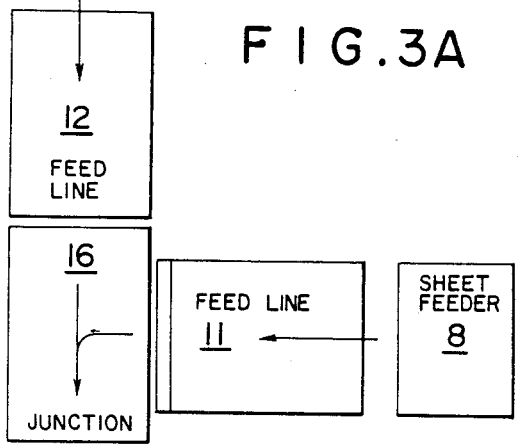
Figure 3B:
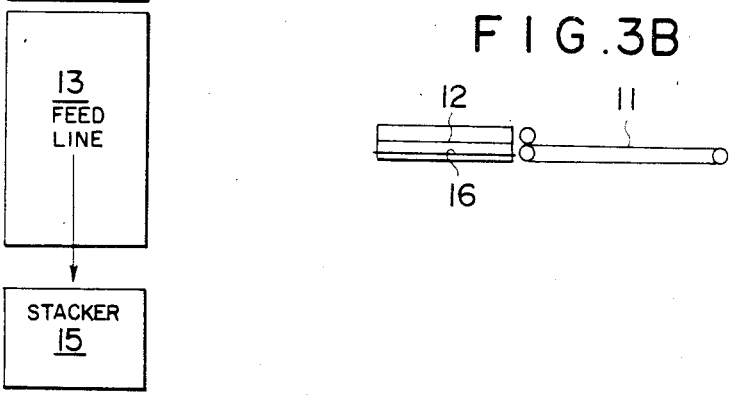

FIGS. 2, 3A and 3B show parts of the system shown in FIG. 1. The stimulable phosphor sheets taken out of the cassettes by the sheet feeder 8 and out of the magazines by the sheet feeder 10 are sent to the junction 16 via the sheet feeding lines 11 and 12. As shown in FIG. 3B, the junction 16 may for example be constituted by a belt conveyor having a height lower than the level of the sheet feeding lines 11 and 12. The phosphor sheets are then conveyed from the junction 16 to the stacker 15 by the sheet feeding line 13 constituted, for example, by a belt conveyor. As shown in FIG. 2, the stacker 15 is provided therein with a stack zone 17, feeding line switching mechanism 18, and a preferential sheet feeding line 19. The feeding line switching mechanism 18 may, for example, be constituted by a movable plate, which is normally set to the position for guiding the phosphor sheets conveyed by the sheet feeding line 13 to the stack zone 17. Accordingly, in normal operations, the phosphor sheets conveyed by the sheet feeding line 13 are passed over the feeding line switching mechanism 18 and fed into the stack zone 17 by a sheet introducing means 20 which may, for example, comprise belts and rollers. The stack zone 17 consists of a number of vertically movable racks, and the phosphor sheets are selectively introduced into empty racks and temporarily stored therein. When the phosphor sheets are to be processed for image reproduction, the stack zone 17 is vertically moved, and the phosphor sheets are selectively ejected by a sheet ejecting means 21 from the stack zone 17 to the sheet feeding line 13 connected to the image read-out apparatus 14, and sent one by one by the sheet feeding line 13 to the apparatus 14. The stack zone 17, the feeding line switching mechanism 18, the sheet introducing means 20, and the sheet ejecting means 21 may be of any types known in the art.

When a phosphor sheet should be preferentially processed for image reproduction, the guide plate of the feeding line switching mechanism 18 is shifted to the side communicating with the preferential sheet feeding line 19 by a signal issued from the general control section 27 upon receiving a preferential processing signal. Accordingly, the phosphor sheet conveyed from the junction 16 by the sheet feeding line 13 is not introduced into the stack zone 17 but directly conveyed on the preferential sheet feeding line 19 and the sheet feeding line 13 to the image read-out apparatus 14.

As described above, the feeding line switching mechanism 18 is controlled by the general control section 27, which also controls the number of the phosphor sheets remaining in the sheet feeders 8 and 10, the number of the phosphor sheets being conveyed on the sheet feeding lines 11, 12 and 13, the number of the phosphor sheets cohtained in the stack zone 17, and the number of the phosphor sheets being conveyed on the preferential sheet feeding line 19. In this way, the general control section 27 receives the preferential processing instructions and controls the system so that the preferential phosphor sheets are sent from the corresponding sheet feeder to the sheet feeding line 13.

In order to selectively activate one of many sheet feeders, the sheet supply ports of the other sheet feeders may be closed, or the phosphor sheets contained in the other sheet feeders may be made to stay therein. If practicable, it is also possible to turn off the electric power for the other sheet feeders. In this way, the phosphor sheets are prevented from becoming stagnant on the sheet feeding line 13 or at the inlet of the stack zone 17.

It should be understood that the present invention can be embodied in various ways other than the above described embodiment. For example, there may be only one or three sheet feeders, the image input stands may be used in combination with image input stands provided with a sheet supplying means or may be replaced by at least one such image input stand. Further, there may be used a plurality of image read-out apparatuses and a plurality of subsequent lines. It is also possible to position the preferential sheet feeding line at the exterior of the stacker.

I claim:

1. A radiation image recording and reproducing system comprising; at least one radiation image input section for recording a radiation image of an object on a stimulable phosphor sheet capable of storing radiation energy thereon by exposure thereof to a radiation passing through the object, an image read-out section for exposing said stimulable phosphor sheet carrying the radiation image stored thereon to a stimulating ray and photoelectrically reading out light emitted from said stimulable phosphor sheet upon stimulation thereof by said stimulating ray to obtain an image signal, an image processing section for processing said image signal sent form said read-out section, an image reproducing section for reproducing the radiation image by use of a reproducing signal sent from said image processing section, at least one sheet supplying means for supplying said stimulable phosphor sheet carrying the radiation image recorded thereon at said radiation image input section to a sheet feeding line connected to said image read-out section, a stack zone positioned on said sheet feeding line for sequentially storing said stimulable phosphor sheets supplied from said sheet supplying means and sending said phosphor sheets one by one to said image read-out section, a radiation image recording and reproducing system provided with a preferential processing function, comprising a by-pass feeding line positioned on said sheet feeding line for by-passing said stack zone, and a feeding line switching mechanism for making said sheet feeding line communicate with said by-pass feeding line in response to a preferential processing signal.

2. A system as defined in claim 1 wherein said radiation image input section comprises a cassette type image input stand for recording the radiation image by use of a cassette containing a single stimulable phosphor sheet.

3. A system as defined in claim 1 wherein said radiation image input section comprises a cassette-less type image input stand for recording the radiation image by use of a magazine containing a plurality of stimulable phosphor sheets.

4. A system as defined in claim 1 wherein said radiation image input section comprises a high-speed image input apparatus for recording the radiation image by use of a magazine containing a plurality of stimulable phosphor sheets.

5. A system as defined in claim 1 wherein said sheet supplying means comprises a sheet feeder for receiving a case containing one or more stimulable phosphor sheets carrying the radiation image or images stored thereon, automatically taking the phosphor sheet or sheets out of the case, and sending the phosphor sheets one by one to said sheet feeding line connected to said image read-out section.

6. A system as defined in claim 1 wherein said sheet feeding line is constituted by a belt conveyor.

7. A system as defined in claim 1 wherein said by-pass feeding line is constituted by a belt conveyor.

8. A system as defined in claim 1 wherein said feeding line switching mechanism comprises a movable guide plate.

9. A system as defined in claim 1 wherein said stack zone comprises a plurality of vertically movable racks.

10. A system as defined in claim 1 wherein said stack zone is provided with a sheet introducing means for introducing said stimulable phosphor sheet from said sheet feeding line to said stack zone via said feeding line switching mechanism, and a sheet ejecting means for ejecting said stimulable phosphor sheet from said stack zone to said sheet feeding line connected to said image read-out section.

11. A system as defined in claim 10 wherein said sheet introducing means and said sheet ejecting means are respectively constituted by belts and rollers.

12. A system as defined in claim 1 wherein said feeding line switching mechanism is controlled by a general control section for controlling said stack zone, said image read-out section and said image processing section.

13. A system as defined in claim 1 wherein said image read-out section is connected to a sorter for sorting the stimulable phosphor sheets returned from said image read-out section according to the sheet sizes.

14. A system as defined in claim 13 wherein said sorted stimulable phosphor sheets are sent to a loader for loading said phosphor sheets into cases for reuse in said radiation image input section.

* * * * *